United States Patent
Igel

[19]

[11] Patent Number: 6,127,268
[45] Date of Patent: Oct. 3, 2000

[54] PROCESS FOR FABRICATING A SEMICONDUCTOR DEVICE WITH A PATTERNED METAL LAYER

[75] Inventor: Guenter Igel, Teningen, Germany

[73] Assignee: Micronas Intermetall GmbH, Freiburg, Germany

[21] Appl. No.: 09/095,986

[22] Filed: Jun. 11, 1998

[30] Foreign Application Priority Data

Jun. 11, 1997 [DE] Germany .......................... 197 24 595

[51] Int. Cl.[7] .................................................. H01L 21/44
[52] U.S. Cl. ......................... 438/678; 438/49; 438/197; 438/668; 438/686
[58] Field of Search .............................. 438/49, 746, 570, 438/575, 580, 584, 758, 759, 686

[56] References Cited

U.S. PATENT DOCUMENTS

| | | | |
|---|---|---|---|
| 3,698,941 | 10/1972 | De Nobel et al. | 117/212 |
| 3,775,192 | 11/1973 | Beale | 148/1.5 |
| 4,321,283 | 3/1982 | Patel et al. | 427/74 |
| 4,442,137 | 4/1984 | Kumar | 427/57 |
| 4,501,768 | 2/1985 | Kumar | 427/57 |
| 4,504,322 | 3/1985 | Adwalpalker et al. | 134/1 |
| 4,703,304 | 11/1987 | Amendola et al. | 427/57 |
| 5,417,821 | 5/1995 | Pyke | 204/153.1 |

OTHER PUBLICATIONS

Vossen and Kern, thin Film Processes, Academic Press, new York, pp. 212–221, 1978.

S. M. Sze, VLSI Technology, McGraw–Hill: New York, p. 382, 1988.

Lundstrom, et al., "A hydrogen–sensitive MOS field–effect transistor", Applied Physics Letters, vol. 26, No. 2, Jan. 15, 1975.

Primary Examiner—Charles Bowers
Assistant Examiner—Erik Kielin
Attorney, Agent, or Firm—Arthur L. Plevy; Buchanan Ingersoll PC

[57] ABSTRACT

A process is disclosed for fabricating a semiconductor device with a patterned metal layer (9). A layer (7) of a material with poor adhesion capability to the metal is deposited on the surface of a semiconductor substrate. On the layer (7), pattern lines (8) separated by a distance a are formed of a material with good adhesion capability to the metal, and the metal layer (9) is deposited such that by suitable choice of the ratio of the distance a to its thickness d and of its material properties, the metal layer (9) is caused to adhere only to the pattern lines (8) and to the area of the layer (7) between the pattern lines (8).

13 Claims, 1 Drawing Sheet

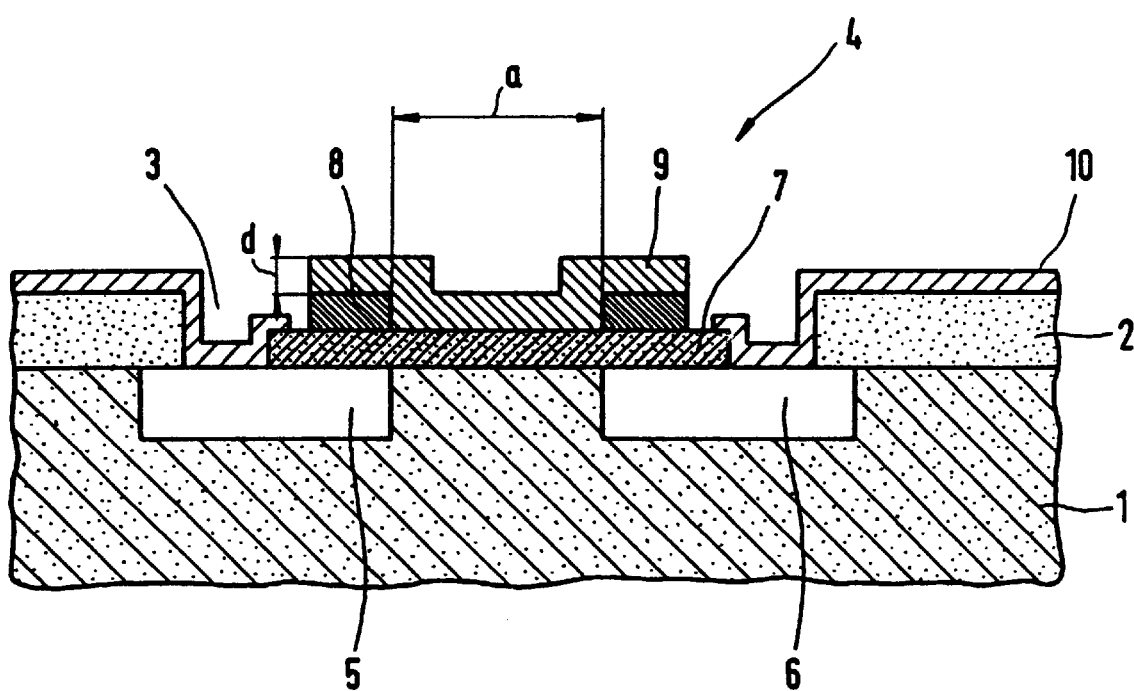

PROCESS FOR FABRICATING A SEMICONDUCTOR DEVICE WITH A PATTERNED METAL LAYER

FIELD OF INVENTION

This invention relates to a process for fabricating a semiconductor device with a patterned metal layer.

BACKGROUND OF INVENTION

In semiconductor technology there are various applications in which it is necessary to deposit patterned metal layers. Metal layers may be required, for example, in predetermined areas on the surface of the semiconductor structure. One example in which a patterned metal layer is deposited is the formation of a metal electrode for a sensor. Such a sensor is known from I. Lundstrom, S. Shivaraman, C. Svensson, and L. Lundkvist, "Hydrogen sensitive MOS field-effect transistor", Appl. Phys. Lett. 26, 55–57. The metal electrodes are commonly formed from noble metals, such as palladium, gold, or platinum.

In practice, the formation of such a patterned metal layer presents particular problems if it is to be deposited on an MOS structure, since the formation of such a layer cannot be combined with the conventional MOS process. After the MOS process, additional process steps would be necessary to deposit the patterned metal layer, particularly photolithographic steps, etching steps, and resist-stripping steps.

If such a metal electrode is deposited on an MOS structure, the process steps required will result in the structure being contaminated by the metal. This will impair the properties of silicon oxide and, in the case of MOS transistors, particularly the properties of the gate oxide, and of the underlying channel. Furthermore, the apparatus used to carry out the process steps in the semiconductor plant will be contaminated, which is not permissible in MOS fabrication. If a metal electrode of a base metal, such as aluminum or titanium, is deposited, these metals will change their properties during fabrication and on contact with other materials. As a result, the characteristics of the sensor will change as well. If platinum is used for the metal electrode, a bonding agent is required, for which titanium is used. In that case, the unfavorable properties described above will occur. Furthermore, the additional steps involved in depositing the metal electrode will make the process complex and costly.

Therefore, it is an object of the invention is to provide an economical process for the fabrication of a semiconductor device with a patterned metal layer.

SUMMARY OF INVENTION

A process for fabricating a semiconductor device with a patterned metal layer (9), said process including the steps of applying to an area of the surface of a semiconductor substrate a layer (7) of a material with poor adhesion capability to the metal, forming on the layer (7) pattern lines (8) of a material with good adhesion capability to the metal which are separated by a distance a, and depositing the metal layer (9) in such a way that by suitable choice of the ratio of the distance a to its thickness d and of its material properties, the metal layer (9) is caused to adhere only to the pattern lines (8) and to the area of the layer (7) between the pattern lines (8).

BRIEF DESCRIPTION OF FIGURES

The sole FIGURE illustrates an embodiment of a device fabricated by the process according to the invention.

DETAILED DESCRIPTION OF INVENTION

This object is attained by a process comprising the steps of: applying to an area of the surface of a semiconductor substrate a layer of a material with poor adhesion capability to the metal, forming pattern lines on the layer which are made of a material with good adhesion capability to the metal and are separated by a distance a, and depositing the metal layer in such a way that by suitable choice of the ratio of the distance a to its thickness d and of its material properties, it is caused to adhere only to the pattern lines and to the area of the layer between the pattern lines.

With the process according to the invention, the metal layer is deposited by suitable choice of its material properties, of the material properties of the pattern lines, and of the geometry, namely the distance between the pattern lines and the thickness of the metal layer. If the metal layer is deposited on an MOS structure, the MOS structure can be produced with the insulating layer and the pattern lines by process steps familiar to those skilled in the art. Only when the MOS process is complete will the semiconductor structure be metallized. No additional mask is necessary, since in the metallizing process, the entire surface of the semiconductor structure is treated, while the metal adheres only to the pattern lines and to the area of the layer between the pattern lines. Outside the pattern lines, the metal layer does not adhere. This is achieved by choosing a suitable value for the distance to a further pattern line or to a feature having a function corresponding thereto.

Since no additional process steps are required for forming the patterned metal layer, the process according to the invention is very simple. In particular, however, it permits the formation of a metal electrode in combination with an MOS process. Since the formation of the patterned metal layer does not require any photolithographic, etching, or resist-stripping steps, the patterned metal layer can be formed from noble metals without the MOS device or the apparatus for carrying out the MOS process being contaminated.

Advantageously, the ratio of the distance a between the pattern lines to the thickness d of the metal layer is greater than 5. At this ratio, the metal layer reliably adheres to the pattern lines and to the area of the insulating layer between the pattern lines, whereas it does not adhere outside the pattern lines. If a slightly greater distance a between the pattern lines is chosen, reliable adhesion of the metal layer to and between the pattern lines can be ensured by increasing the thickness d of the metal layer. The distance a is preferably less than 10 μm.

In a preferred embodiment of the invention, the metal layer is formed by vapor deposition of a metal and subsequent selective, material-dependent removal of the metal layer by means of ultrasound. If the thickness d, the distance a, the material of the pattern lines, and the metal are chosen appropriately, the vapor-deposited metal outside the pattern lines with the predetermined separation a will be reliably removed by the ultrasonic treatment and will reliably adhere to the pattern lines and between the pattern lines. Adhesion of the metal layer between the pattern lines is ensured, despite the poor adhesion capability of the insulating layer to the metal, by the geometry of the pattern lines with good adhesion capability to the metal.

The deposition of the patterned metal layer requires no process steps that could adversely affect the semiconductor structure, particularly if the latter includes MOS devices. Expensive masking steps are not necessary, either.

Advantageously, a noble metal, particularly palladium, is used for the metal layer. Selective adhesion of the palladium to the pattern lines and to the layer between the pattern lines is very reliable. Prior to its selective removal, the metal layer is advantageously treated with a hydrogen-containing gas. Then the selective removal of the metal layer will be more reliable and faster.

In another embodiment of the invention, the metal layer is deposited by plating, particularly by electroless plating. The material of the pattern lines and the metal must then be chosen appropriately. Between the pattern lines, the metal adheres because of the geometry chosen. If electroless plating is used, the metal to be deposited must be more noble than the material of the pattern lines.

In a preferred embodiment of the invention, an MOS transistor is formed on the semiconductor substrate, and the layer is applied as the gate insulating layer of the MOS transistor, on which a polysilicon layer is formed in such a way as to form gate electrodes corresponding to the pattern lines and separated by the distance a. In this embodiment, the MOS transistor can be used as a sensor. In that case, the gate insulating layer may be made of silicon oxide, the pattern lines of polysilicon, and the patterned metal layer, which serves as the gate, of palladium.

The invention will now be explained in more detail with reference to the accompanying drawing.

The single figure of the drawing shows an embodiment of a device fabricated by the process according to the invention. The semiconductor device shown represents a sensor in MOS technology. A semiconductor substrate 1 is covered by a field oxide layer 2. In an opening 3 of field oxide layer 2, an MOS transistor 4 acting as a sensor was formed. MOS transistor 4 comprises a drain region 5, a source region 6, and a gate region. The latter comprises a layer 7, which is an insulating layer. Deposited on layer 7 are pattern lines 8, which form gate electrodes of the transistor and are separated by a distance a. Pattern lines 8 and the area of layer 7 between pattern lines 8 are covered by a metal layer 9 of thickness d. The material of layer 7 has poor adhesion capability to the metal of metal layer 9, and the material of pattern lines 8 has good adhesion capability to the metal of metal layer 9. In a preferred embodiment, layer 7 may be made of silicon oxide, pattern lines 8 of polysilicon, and metal layer 9 of palladium, for example. To make contact to drain region 5 and source region 6, contact lines 10 were deposited.

The ratio of the distance a between pattern lines 8 to the thickness d of metal layer 9 is preferably greater than 5, and the distance a between pattern lines 8 is less than 10 μm. The bond between metal layer 9 and pattern lines 8 is secured by suitable choice of material properties, and the adhesion of metal layer 9 to the area of layer 7 between pattern lines 8 is achieved by suitable choice of the geometry and by means of the bond between layer 7 and pattern lines 8. The adhesion to layer 7 is thus achieved without the need for a material with good adhesion capability to the metal.

In the following, the process according to the invention will be described with the aid of the sole figure. Using process steps familiar to those skilled in the art, the field oxide layer 2 with the opening 3 and the MOS transistor 4 in the opening 3 are formed on the semiconductor substrate 1. The fabrication, including the formation of layer 7, takes place in a conventional manner. The pattern lines 8 are also formed with process steps commonly employed in MOS technology.

Then, in a first embodiment of the invention, the metal for metal layer 9 is deposited over the entire surface of the semiconductor structure by evaporation. The metal layer thus formed must be selectively removed. This is done by subjecting the semiconductor structure to an ultrasonic treatment which removes the metal layer from the surface of the semiconductor structure outside the pattern lines 8. Prior to the ultrasonic treatment, the semiconductor structure may be treated with a hydrogen-containing gas. For the metal layer, palladium may be used. Since palladium absorbs hydrogen, this treatment results in easier detachment of the metal layer from the surface of the semiconductor structure outside the pattern lines 8. The adhesion capabilities of the polysilicon of pattern lines 8 and the palladium are such that the palladium layer will adhere to the silicon even during the ultrasonic treatment. Because of the selected ratio of the distance a between pattern lines 8 to the thickness d of metal layer 9, the metal layer also continues to adhere to layer 7 in the area between the pattern lines. Because of the geometry chosen, this adhesion will persist even if layer 7 is made of a material with poor adhesion capability to the metal of metal layer 9. In particular, palladium will continue to adhere to an insulating layer, which may be made of silicon oxide for example.

In a second embodiment of the process according to the invention, metal layer 9 is deposited by plating, particularly by electroless plating, in such a way as to adhere only to pattern lines 8 and to the area of layer 7 between pattern lines 8. In this embodiment, too, adhesion to pattern lines 8 is secured by appropriate selection of the materials of pattern lines 8 and metal layer 9, and adhesion to the area of layer 7 between pattern line 8 is achieved by suitable choice of the geometry. In this embodiment it is essential that the metal to be deposited be a more noble metal than the material of pattern lines 8.

Although the invention has been described in preferred and alternative forms with a certain degree of particularity, it is understood that the present disclosure of the preferred and alternative forms has been made only by way of example, and that numerous changes in the details of construction and combination and arrangement of parts may be made without departing from the spirit and scope of the invention as hereinafter claimed. It is intended that the patent shall cover by suitable expression in the appended claims, whatever features of patentable novelty exist in the invention disclosed.

What is claimed is:

1. A process for fabricating a semiconductor device with a patterned metal layer, said process comprising the steps of:

applying a layer (7) of material to an area of the surface of a semiconductor substrate;

forming pattern lines (8) of material on the layer (7), the pattern lines (8) separated by a distance a, wherein the distance a <10 μm;

forming a noble metal layer (9) to a thickness d on the semiconductor substrate, wherein a/d>5, the layer (7) of material having substantially no propensity for adhering to the noble metal layer (9), the pattern lines (8) having a substantial propensity for adhering to the noble metal layer (9); and selectively removing the noble metal layer (9) outside the pattern lines (8) using ultrasound wherein the ratio of the distance a between the pattern lines (8) to the thickness d of the noble metal layer (9), and the propensity of the pattern lines (8) for adhering to the noble metal layer (9), causes the noble metal layer (9) to adhere only to the pattern lines (8) and to the area of the layer (7) between the pattern lines (8).

2. The process of claim 1, wherein palladium is used for the noble metal layer (9).

3. The process of claim 1, wherein the noble metal layer (9) is deposited by electroless plating.

4. The process of claim 1, wherein the noble metal layer (9) is formed by vapor deposition of a noble metal.

5. The process of claim 4, wherein prior to the selective removal, the metal layer (9) is treated with a hydrogen-containing gas.

6. The process of claim 1, wherein an MOS transistor is formed on the semiconductor substrate, and that the layer (7) is applied as the gate-insulating layer of said MOS transistor, on which a polysilicon layer is formed in such a way as to form gate electrodes corresponding to the pattern lines (8) and separated by the distance a.

7. A method for fabricating a semiconductor device, said method comprising the steps of:

providing a semiconductor substrate having a transistor formed therein;

forming a layer (7) of material on an area of the surface of the semiconductor substrate, the layer (7) having an opening above the transistor;

forming pattern lines (8) of material on the layer (7), the pattern lines (8) separated by a distance a, wherein the distance a <10 $\mu$m;

depositing a layer (9) of a noble metal to a thickness d on the semiconductor substrate, wherein a/d>5, the layer (7) having substantially no propensity for adhering to the noble metal layer (9), the pattern lines (8) having a substantial propensity for adhering to the noble metal layer (9); and ultrasonically patterning the noble metal layer (9);

wherein the ratio of the distance a between the pattern lines (8) to the thickness d of the noble metal layer (9), and the propensity of the pattern lines (8) for adhering to the noble metal layer (9), causes the noble metal layer (9) to adhere only to the pattern lines (8) and to the area of the layer (7) between the pattern lines (8).

8. The method of claim 7, wherein before said step of ultrasonically patterning further comprising the step of treating said semiconductor structure to facilitate said patterning of said metal layer.

9. The method of claim 8, wherein said treating comprises utilizing a hydrogen-containing gas.

10. The method of claim 8, wherein said noble metal is palladium.

11. The method of claim 7, wherein said transistor comprises:

a drain region;

a source region; and a gate region formed by said layer (7) of material and said pattern lines (8).

12. The method of claim 11, wherein said pattern lines comprise polysilicon.

13. The method of claim 12, wherein said layer (7) of material comprises silicon dioxide.

* * * * *